(12) United States Patent
Vartiainen et al.

(10) Patent No.: US 6,652,812 B1
(45) Date of Patent: Nov. 25, 2003

(54) SPECIMEN TUBE

(75) Inventors: Ilkka Vartiainen, Kuopio (FI); Pasi Ikonen, Kuopio (FI); Fabrizio Galbiati, Kuopio (FI)

(73) Assignee: Clids Oy, Kuopio (FI)

( * ) Notice: Subject to any disclaimer, the term of this patent is extended or adjusted under 35 U.S.C. 154(b) by 0 days.

(21) Appl. No.: 09/482,617

(22) Filed: Jan. 14, 2000

Related U.S. Application Data

(63) Continuation of application No. PCT/FI98/00583, filed on Jul. 10, 1998.

(30) Foreign Application Priority Data

Jul. 16, 1997 (FI) .................................................. 973015

(51) Int. Cl.$^7$ ................................................ B01L 3/00
(52) U.S. Cl. ...................... 422/102; 422/99; 422/103; 422/104
(58) Field of Search ............................... 422/62–67, 99, 422/100, 102, 913, 915, 917; 436/43–48, 180

(56) References Cited

U.S. PATENT DOCUMENTS

| | | | | |
|---|---|---|---|---|
| 3,619,568 A | * | 11/1971 | Taplin | 235/61.9 |
| 3,754,872 A | * | 8/1973 | Zauft | 23/292 |
| 3,778,790 A | * | 12/1973 | Prost et al. | 340/174.1 |
| 3,781,120 A | * | 12/1973 | Engelhardt | 356/244 |
| 3,818,188 A | * | 6/1974 | Hertel et al. | 235/61.11 |
| 5,350,564 A | * | 9/1994 | Mazza et al. | 422/63 |
| 5,651,941 A | * | 7/1997 | Stark et al. | 422/104 |
| 5,777,303 A | * | 7/1998 | Berney | 235/375 |
| 5,893,263 A | * | 4/1999 | Matsumoto et al. | 156/387 |
| 6,083,462 A | * | 7/2000 | Ikonen et al. | 422/104 |
| 6,085,603 A | * | 7/2000 | Riekkinen | 73/864.21 |
| 6,190,615 B1 | * | 2/2001 | Cocola et al. | 422/102 |

FOREIGN PATENT DOCUMENTS

WO    WO 89/08264    9/1989

* cited by examiner

*Primary Examiner*—Jill Warden
*Assistant Examiner*—Dwayne K. Handy
(74) *Attorney, Agent, or Firm*—Pillsbury Winthrop LLP

(57) ABSTRACT

The invention relates to a sampling tube to which is fastened a memory device which is used to record data used to identify said sampling tube and/or its contents and the memory device being fastened to said sampling tube with a mounting piece. A mounting piece in accordance with the invention has a part which remains on the sampling tube or its part when the electronic memory device is attached to the sampling tube and/or detached from the sampling tube.

3 Claims, 2 Drawing Sheets

SPECIMEN TUBE

Figure 1:
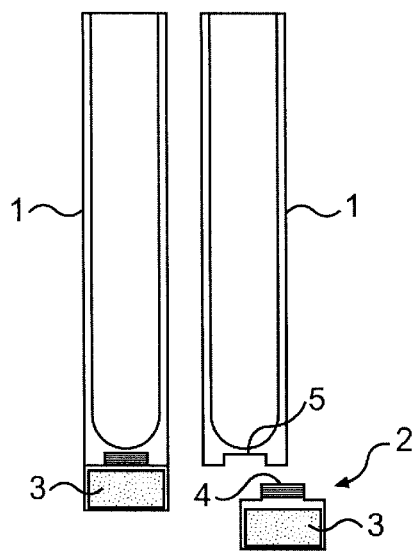

This Application is a Continuation of International Application No. PCT/FI98/00583 filed Jul. 10, 1998.

The invention relates to a sampling tube, to which is fastened a memory device which records data used to identify said sampling tube and/or its contents, and the memory device being fastened to said sampling tube with a mounting piece.

Sampling tubes are used in different laboratories, research institutes or corresponding varying research and/or used for experimental work with and conveyance and preservation of stored samples or test solutions. It is a common practice to connect an electronic memory device to a sampling tube. With the aid of such a memory device, data about the contents of the sampling tube can be saved into the computer memory. Processes can be observed, completed measurements and activity within the sampling tube can be recorded to the memory. In this way, all of the different process stages of the tube and its contents can be monitored.

At present, the problem with such an electronic memory device, is that it easily detaches from the sampling tube. The problem is, that in moving and handling the sampling tube, in some circumstances, the memory device can accidentally detach from the sampling tube. In such an instance, the contents of the sampling tube are worthless and cannot be handled further. The fact that the memory device has fallen off, due to the structure of the mounting piece, may not immediately be noticed. A memory device can be re-attached to a sampling tube, but whether or not a device has been re-attached to the right sampling tube remains undetermined. It is also possible for memory devices and sampling tubes to be switched intentionally, because a memory device can be re-attached to a sampling tube. Currently, people who use sampling tubes have no way whatsoever of knowing if a sampling tube has had a memory device attached to it, or if a memory device actually matches the contents of the tube it is attached to.

The invention seeks to provide a sampling tube, in which the preceding disadvantages will be eliminated. Specifically, the invention seeks to provide a sampling tube, from which the user can quickly and easily determine whether or not said tube has been handled and whether or not a memory device has previously been attached to it. Further, the invention seeks to provide a sampling tube to which only one memory device can be attached.

In accordance with the invention, the objective is accomplished by a sampling tube, the characteristics of which are set forth in the patent claim.

A sampling tube, in accordance with the invention, has a mounting piece which is designed so that when the electronic memory device is attached or detached, part of the mounting piece remains permanently attached to the sampling tube. When such a sampling tube is used and a memory device has been attached to it, if the memory device falls off or becomes detached, it will leave this piece behind as a mark on the sampling tube. Although a second memory device may be attached to the sampling tube, the mark from the previous memory device will not be covered, as that it can be noted later. This means that this same sampling tube can also be used later, but it can be determined from the sampling tube that it has been used earlier. Memory devices can be used several times on different sampling tubes as a mounting piece.

One advantageous application of the invention is that it has a mounting piece which is made with a part which breaks off of the mounting and fits into the sampling tube or some other part of the sampling tube, so that no other memory device may be attached to the sampling tube. In this way, the sampling tube is so disfigured that no other electronic memory device can be attached to it. The sampling tube is a disposable tube, but the memory device can be used again with other sampling tubes.

Another advantageous application of the invention is that the mounting piece has an implement with which the electronic memory device is mounted to and/or removed from the sampling tube. In this case, the implement and/or other mounting piece is designed such that it does not cause breakage in the sampling tube's structure. The mark which is left can also be such that the implement causes breakage in the sampling tube's structure.

The structure and form of the mounting piece, which causes the mark to be left, can vary considerably in the various applications of the invention. It can be joined between the sampling tube and memory device, such as a mounting part in the sampling tube which breaks off or some other part of the sampling tube which can break off, a memory device with a mounting element which leaves a visible mark on the surface of the sampling tube or mounting pieces which are separate from the sampling tube and memory device.

The invention will now be described in more detail with reference to the accompanying drawings, in which, FIGS. 1–6 present different applications to the sampling tube, which use different mounting pieces on the memory device in order to fasten it to the sampling tube. The drawings are cross-sections and profiles.

FIG. 1 illustrates a sampling tube 1 to which an electronic memory device 3 has been or may be attached. The mounting piece 2 is a protruding plug 4, the exterior of which has been made with a screw thread. The bottom part 5 of the sampling tube 1 is formed with a depression, which has a depth corresponding to the height of the protruding plug and it has been made with an inner screw thread. The threads are designed and made such that the thread on the inside of the tube will break either when the memory device is being screwed in, or when it is being loosened, so that no other memory device can be attached to the sampling tube. This can be done, for instance, by making the thread in the sampling tube of a different material than the thread on the plug and also by making threads which are suited for this purpose.

Figure 2:
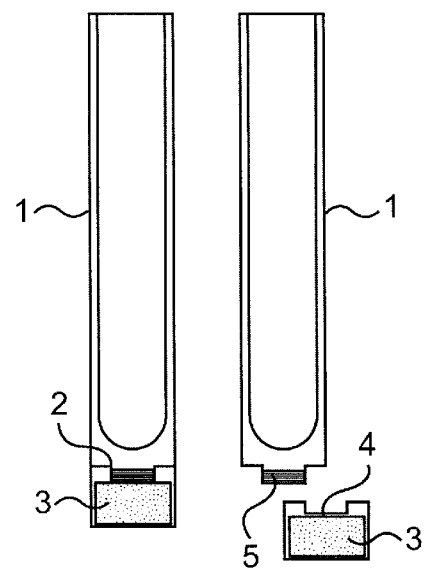

FIG. 2 illustrates a memory device 3, which has been made with a depression 4, which has an inner screw thread. Sampling tube 1 is formed with a protruding plug 5 with an outer screw thread corresponding to that of the depression. The thread in the sampling tube is also such that it breaks when the memory device is being attached or removed.

Figure 3:
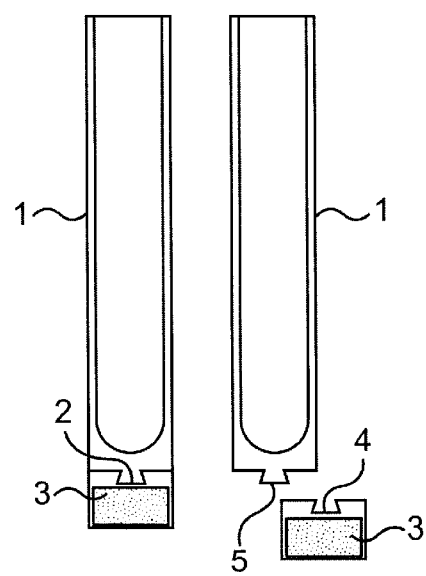
Figure 4:
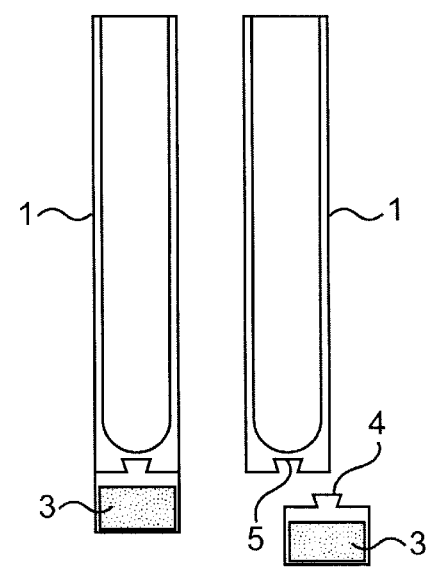

FIGS. 3 and 4 illustrate a mounting structure 2 in the form of a protruding peg and a depression in the configuration of the peg. The protruding peg narrows upwardly from the bottom of the tube while the corresponding depression widens downwardly from the surface of the mounting piece. In FIG. 3, the protruding peg 5 is formed on the bottom of the sampling tube 1 and the depression 4 is formed on top of the memory device 3. In FIG. 4, the parts are reversed, in other words, the protruding peg 4 is on top of the memory device 3 and its corresponding depression 5 is on the bottom of the sampling tube 1. In both cases, the materials chosen are such that part 5 on the sampling tube 1 will break when the memory device 3 is loosened.

Figure 5:
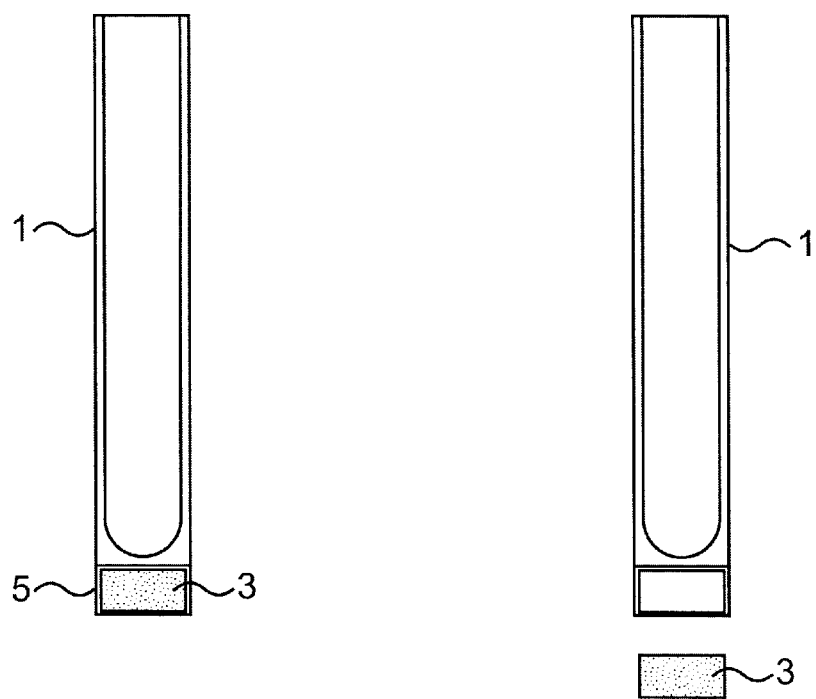

FIG. 5 illustrates a memory device 3 secured inside a small case 5 on the bottom of the sampling tube 1. The lid 4 of the case can be loosened from the sampling tube, but in order to detach it, it is necessary to break either the case lid or the edges, either manually or using a special implement.

Figure 6:
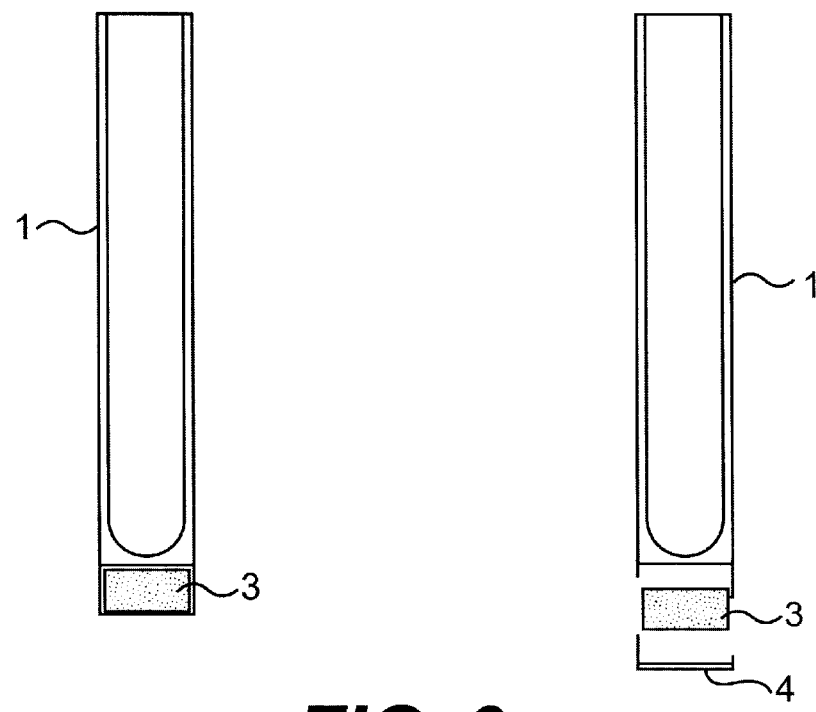

FIG. 6 also illustrates a memory device secured in a small case 5 on the bottom of the sampling tube 1. The design of this case is different from that of the preceding and the side of the case breaks off if the identifying memory is detached.

The memory device can also be mounted to the sampling tube in other ways. For example, glue can be used to seal the connection, in which case the seal would have to be broken if the memory device were to be detached. The broken seal would leave a clear mark on the test tube. Further, the mounting can be secured using tape or an adhesive sticker. This kind of mounting will also leave a clear mark on the tube. One alternative is to cover part of the sampling tube with a suitable material which will show that the sampling tube has been used. In this case, in FIG. 1 or 4, for example, a membrane can be attached to the bottom part of the sampling tube which is removed or broken when the memory device is mounted.

The invention is not limited to the advantageous application set forth in this application. The invention is versatile and its form can vary within the frame of the idea of the invention put forth in the patent claim.

What is claimed is:

1. A specimen tube comprising:

a sampling tube; and a memory device configured to be fastened to said sampling tube and to record data used to identify at least one of said sampling tube and its contents;

wherein said memory device comprises a mounting piece to fasten said memory device to said sampling tube; and wherein said mounting piece has a part which remains on said sampling tube when the electronic memory device is detached from the sampling tube.

2. The specimen tube as claimed in claim 1, wherein said part of said mounting piece is designed such that it breaks off at a point of connection in the sampling tube so that an electronic memory device may not be attached again to said sampling tube.

3. The specimen tube as claimed in claim 1, wherein said mounting piece comprises a threaded body, by which said electronic memory device is fastened to said sampling tube.

* * * * *